(12) United States Patent
Yevzlin et al.

(10) Patent No.: US 9,597,443 B2
(45) Date of Patent: Mar. 21, 2017

(54) ANASTOMOTIC CONNECTOR

(75) Inventors: Alexander S. Yevzlin, Black Earth, WI (US); Reed A. Houge, Buffalo, MN (US); Jeff M. Welch, Maple Grove, MN (US); Doug S. Wahnschaffe, Rogers, MN (US); Steve Berhow, Rogers, MN (US)

(73) Assignee: PHRAXIS, INC., St. Paul, MN (US)

( * ) Notice: Subject to any disclaimer, the term of this patent is extended or adjusted under 35 U.S.C. 154(b) by 521 days.

(21) Appl. No.: 14/119,652

(22) PCT Filed: Jun. 15, 2012

(86) PCT No.: PCT/US2012/042666
§ 371 (c)(1),
(2), (4) Date: Nov. 22, 2013

(87) PCT Pub. No.: WO2012/174376
PCT Pub. Date: Dec. 20, 2012

(65) Prior Publication Data
US 2014/0100510 A1    Apr. 10, 2014

Related U.S. Application Data

(60) Provisional application No. 61/497,245, filed on Jun. 15, 2011, provisional application No. 61/497,254, filed on Jun. 15, 2011.

(51) Int. Cl.
*A61M 5/00*  (2006.01)
*A61M 1/36*  (2006.01)
*A61B 17/11*  (2006.01)

(52) U.S. Cl.
CPC ........... *A61M 1/3653* (2013.01); *A61B 17/11* (2013.01); *A61M 1/3655* (2013.01); *A61B 2017/1107* (2013.01); *A61B 2017/1135* (2013.01)

(58) Field of Classification Search
CPC .... A61B 17/11; A61M 1/3653; A61M 1/3655
(Continued)

(56) References Cited

U.S. PATENT DOCUMENTS 3,818,511 A   6/1974  Goldberg et al.
4,352,358 A  10/1982  Angelchik
(Continued)

FOREIGN PATENT DOCUMENTS

CA   2366703 A1   9/2000
CA   2574941 A1   7/2007
(Continued)

OTHER PUBLICATIONS

Japanese Final Rejection Office Action, issued by the Japanese Patent Office regarding corresponding patent application Serial No. JP 2014-516024; mailed dated Jun. 4, 2015; 5 pages.
(Continued)

*Primary Examiner* — Philip R Wiest
(74) *Attorney, Agent, or Firm* — Fox Rothschild LLP

(57) ABSTRACT

An anastomotic connector comprises a generally tubular access port having a first end and a second end, a generally tubular main body portion having a first end and a second end, wherein the second end of the main body portion is positioned adjacent to the second end of the access port such that the main body portion and access port are in fluid communication, and an anchor member received, within the access port and having a plurality of fingers that are extendable from the first end thereof. The fingers of the anchor member are movable between a loaded position wherein the fingers are substantially parallel to a center axis of the access port and an expanded position wherein the fingers are substantially perpendicular to the center axis of the access port.

27 Claims, 7 Drawing Sheets

(58) Field of Classification Search
USPC .................................................. 606/153–155
See application file for complete search history.

(56) References Cited

U.S. PATENT DOCUMENTS

| | | | |
|---|---|---|---|
| 4,368,736 | A | 1/1983 | Kaster |
| 4,512,761 | A | 4/1985 | Raible |
| 5,456,712 | A | 10/1995 | Maginot |
| 5,755,775 | A | 5/1998 | Trerotola |
| 5,755,778 | A | 5/1998 | Kleshinski |
| 5,968,089 | A | 10/1999 | Krajicek |
| 5,972,017 | A | 10/1999 | Berg et al. |
| 6,030,395 | A | 2/2000 | Nash et al. |
| 6,179,848 | B1 | 1/2001 | Solem |
| 6,190,590 | B1 | 2/2001 | Randall et al. |
| 6,210,429 | B1 | 4/2001 | Vardi et al. |
| 6,241,743 | B1 | 6/2001 | Levin et al. |
| 6,270,524 | B1 | 8/2001 | Kim |
| 6,293,955 | B1 * | 9/2001 | Houser ............... A61B 17/11 606/153 |
| 6,402,767 | B1 | 6/2002 | Nash et al. |
| 6,451,048 | B1 | 9/2002 | Berg et al. |
| 6,458,140 | B2 | 10/2002 | Akin et al. |
| 6,464,665 | B1 | 10/2002 | Heuser |
| 6,464,709 | B1 | 10/2002 | Shennib et al. |
| 6,482,214 | B1 | 11/2002 | Sidor et al. |
| 6,485,513 | B1 | 11/2002 | Fan |
| 6,517,558 | B2 | 2/2003 | Gittings et al. |
| 6,582,463 | B1 | 6/2003 | Mowry et al. |
| 6,585,760 | B1 | 7/2003 | Fogarty |
| 6,599,303 | B1 | 7/2003 | Peterson et al. |
| 6,648,901 | B2 * | 11/2003 | Fleischman ............ A61B 17/11 606/155 |
| 6,682,540 | B1 | 1/2004 | Sancoff et al. |
| 6,719,781 | B1 | 4/2004 | Kim |
| 6,743,243 | B1 | 6/2004 | Roy et al. |
| 6,855,162 | B2 | 2/2005 | Parodi |
| 7,025,773 | B2 | 4/2006 | Gittings et al. |
| 7,056,326 | B2 | 6/2006 | Bolduc et al. |
| 7,105,020 | B2 | 9/2006 | Greenberg et al. |
| 7,175,652 | B2 | 2/2007 | Cook et al. |
| 7,267,680 | B2 | 9/2007 | Wright |
| 7,591,827 | B2 | 9/2009 | Hill et al. |
| 7,611,523 | B2 | 11/2009 | Vargas et al. |
| 7,691,140 | B2 | 4/2010 | Bates et al. |
| 7,722,665 | B2 | 5/2010 | Anwar et al. |
| 7,766,955 | B2 | 8/2010 | Vardi et al. |
| 7,828,834 | B2 | 11/2010 | Garbe |
| 7,850,725 | B2 | 12/2010 | Vardi et al. |
| 7,892,247 | B2 | 2/2011 | Conston et al. |
| 7,927,343 | B2 | 4/2011 | Hill et al. |
| 8,287,586 | B2 | 10/2012 | Schaeffer et al. |
| 8,298,251 | B2 | 10/2012 | Golden et al. |
| 8,343,204 | B2 | 1/2013 | Osborne |
| 8,361,092 | B1 | 1/2013 | Asfora |
| 8,366,651 | B2 | 2/2013 | Dakin et al. |
| 8,439,963 | B2 | 5/2013 | Dickinson et al. |
| 8,486,153 | B2 | 7/2013 | Levine et al. |
| 8,551,127 | B2 | 10/2013 | Asfora et al. |
| 8,628,583 | B2 | 1/2014 | Meade et al. |
| 8,715,336 | B2 | 5/2014 | Chu et al. |
| 8,728,145 | B2 | 5/2014 | Chuter et al. |
| 2002/0022853 | A1 | 2/2002 | Swanson et al. |
| 2002/0099392 | A1 | 7/2002 | Mowry et al. |
| 2002/0099393 | A1 * | 7/2002 | Fleischman ............ A61B 17/11 606/153 |
| 2002/0123790 | A1 | 9/2002 | White et al. |
| 2003/0109893 | A1 | 6/2003 | Vargas et al. |
| 2003/0144578 | A1 | 7/2003 | Koster, Jr. |
| 2003/0176878 | A1 * | 9/2003 | Bolduc ............... A61B 17/0469 606/153 |
| 2003/0216749 | A1 | 11/2003 | Ishikawa et al. |
| 2004/0102794 | A1 | 5/2004 | Roy et al. |
| 2004/0107004 | A1 | 6/2004 | Levine et al. |
| 2004/0116946 | A1 | 6/2004 | Goldsteen et al. |
| 2004/0133221 | A1 | 7/2004 | Sancoff et al. |
| 2005/0137677 | A1 | 6/2005 | Rush |
| 2005/0171598 | A1 | 8/2005 | Schaeffer |
| 2005/0192604 | A1 | 9/2005 | Carson et al. |
| 2005/0228409 | A1 | 10/2005 | Coppi |
| 2005/0267559 | A1 | 12/2005 | De Oliveira |
| 2007/0073388 | A1 | 3/2007 | Krolik et al. |
| 2007/0106313 | A1 | 5/2007 | Golden et al. |
| 2007/0179590 | A1 | 8/2007 | Lu et al. |
| 2007/0185567 | A1 | 8/2007 | Heuser et al. |
| 2007/0203572 | A1 | 8/2007 | Heuser et al. |
| 2007/0293940 | A1 | 12/2007 | Schaeffer et al. |
| 2008/0082159 | A1 | 4/2008 | Tseng et al. |
| 2008/0154290 | A1 * | 6/2008 | Golden ............... A61B 17/0644 606/153 |
| 2008/0288044 | A1 | 11/2008 | Osbourne |
| 2009/0030502 | A1 | 1/2009 | Sun et al. |
| 2009/0036817 | A1 | 2/2009 | Dakin et al. |
| 2009/0076587 | A1 | 3/2009 | Cully et al. |
| 2009/0143793 | A1 | 6/2009 | Chua et al. |
| 2009/0209855 | A1 | 8/2009 | Drilling et al. |
| 2010/0010613 | A1 | 1/2010 | Dorn |
| 2010/0036401 | A1 | 2/2010 | Navia |
| 2010/0241218 | A1 | 9/2010 | Bruszewski et al. |
| 2010/0280612 | A1 | 11/2010 | Helmus |
| 2011/0031656 | A1 | 2/2011 | Anneaux et al. |
| 2011/0118821 | A1 | 5/2011 | Brocker et al. |
| 2011/0172684 | A1 | 7/2011 | Granja Filho |
| 2011/0264196 | A1 | 10/2011 | Savage et al. |
| 2011/0282368 | A1 | 11/2011 | Swayze et al. |
| 2012/0065652 | A1 | 3/2012 | Cully |
| 2012/0123513 | A1 | 5/2012 | Asfora et al. |
| 2012/0290065 | A1 | 11/2012 | Li et al. |
| 2013/0035752 | A1 | 2/2013 | Chang |
| 2013/0274646 | A1 | 10/2013 | Paris et al. |
| 2014/0031785 | A1 | 1/2014 | Schwagten et al. |
| 2014/0121585 | A1 | 5/2014 | Baker et al. |

FOREIGN PATENT DOCUMENTS

| | | |
|---|---|---|
| CA | 2766347 A1 | 12/2010 |
| CA | 2810671 | 3/2012 |
| JP | 2004-516914 A | 8/2002 |
| JP | 2006-510393 A | 2/2004 |
| JP | 2006-523515 A | 10/2006 |
| WO | WO 98-02099 A1 | 1/1998 |
| WO | WO-98-19629 A2 | 5/1998 |
| WO | WO-98-19636 A2 | 5/1998 |
| WO | WO 99-45861 A1 | 9/1999 |
| WO | WO 99-62415 A1 | 12/1999 |
| WO | WO 01-12074 A1 | 2/2001 |
| WO | WO 01-26562 A1 | 4/2001 |
| WO | WO 01-49213 A2 | 7/2001 |
| WO | WO 01-49213 A3 | 7/2001 |
| WO | WO-2004-010898 A1 | 2/2004 |
| WO | WO-2004-093966 A1 | 11/2004 |
| WO | WO 2006-028925 A1 | 3/2006 |
| WO | WO 2007-024964 A1 | 3/2007 |
| WO | WO 2008-0157283 A1 | 12/2008 |
| WO | WO-2009-055651 A1 | 4/2009 |
| WO | WO 2010-121192 A1 | 10/2010 |
| WO | WO 2012-034108 A1 | 3/2012 |
| WO | WO 2012-117402 A1 | 9/2012 |

OTHER PUBLICATIONS

Japanese Final Rejection Office Action, issued by the Japanese Patent Office regarding corresponding patent application Serial No. JP 2014-514937; dated Jun. 10, 2015; 7pages.

Japanese Rejection Office Action, issued by the Japanese Patent Office regarding corresponding patent application Serial No. JP 2014-516037; dated Jun. 4, 2015; 8 pages.

International Search Report, issued by the United States Receiving Office, corresponding patent application Serial No. PCT/US2012/042666; mailed Sep. 13, 2012; 2 pages.

(56) References Cited

OTHER PUBLICATIONS

European Search Report issued by the European Patent Office, regarding correspondence patent application Serial No. 12799745.0; dated Feb. 12, 2015; 6 pages.
European Search Report issued by the European Patent Office, regarding correspondence patent application Serial No. 12800430.6; dated Feb. 17, 2015; 6 pages.
European Search Report issued by the European Patent Office regarding correspondence patent application Serial No. 12800335.7; dated Mar. 6, 2015; 6 pages.
International Search Report and Written Opinion issued by the ISA/U.S. Receiving Office, regarding corresponding application Serial No. PCT/US2012/042639; dated Sep. 25, 2012; 9 pages.
International Search Report and Written Opinion issued by the ISA/U.S. Receiving Office, regarding corresponding application Serial No. PCT/US2012/042688; dated Sep. 14, 2012; 9 pages.
International Search Report and Written Opinion issued by the ISA/U.S. Receiving Office, regarding corresponding application Serial No. PCT/US2012/067561; dated Apr. 22, 2013; 10 pages.
Japanese Rejection Office Action, issued by the Japanese Patent Office regarding corresponding patent application Serial No. 2015-517230; mailed Nov. 16, 2015; 8 pages (English translation).
Japanese Office Action issued by the Japanese Patent Office (translated), regarding corresponding patent application Serial No. 2014-516024, mailed Oct. 15, 2014; 5 pages.
Japanese Office Action issued by the Japanese Patent Office (translated), regarding corresponding patent application Serial No. 2014-514937, mailed Oct. 15, 2014; 6 pages.
Japanese Office Action issued by the Japanese Patent Office (translated), regarding corresponding patent application Serial No. 2014-516037, mailed Oct. 15, 2014; 5 pages.

\* cited by examiner

ANASTOMOTIC CONNECTOR

CROSS REFERENCE TO RELATED APPLICATIONS

This application is a U.S. national stage application of International application Ser. No.: PCT/US2012/042666, filed on Jun. 15, 2012, which claims priority to U.S. application Ser. No.: 61/497,245, filed on Jun. 15, 2011, and U.S. application Ser. No.: 61/497,254, filed on June 15, 2011, the entireties of which are hereby incorporated by reference.

BACKGROUND OF THE INVENTION

Field of the Invention

This invention relates to anastomotic connector devices. In particular, this invention relates to a vascular access device for use in hemodialysis and other procedures, such as in the cardiovascular field, where short-term and long-term access is required.

Description of the Related Art

In the United States alone, approximately 400,000 people have end-stage renal disease requiring chronic hemodialysis. Hemodialysis replaces kidney function by removing toxins from the blood that are normally removed by healthy kidneys. In order to effectively remove toxins, blood must be passed at a high blood flow rate through a hemodialysis machine. This high blood flow is best achieved by the creation of a permanent vascular access site that includes an arteriovenous (AV) anastomosis in which a vein is attached to an artery to form a high-flow shunt or fistula.

Typically, a vein may be directly attached to an artery, but it takes from six to eight weeks before the fistula has sufficiently matured (time between placement and cannulation for dialysis) to provide adequate blood flow for use with hemodialysis. Moreover, a direct anastomosis may not be feasible in all patients due to anatomical considerations. Other patients may require the use of artificial graft material to provide an access site between the arterial and venous vascular systems. Because of the length of time required for a fistula to mature a patient needing dialysis will typically require a temporary access device, such as a Quinton catheter, to be inserted for hemodialysis access until the fistula has matured. The use of a temporary catheter access exposes the patient to additional risk of bleeding and infection, as well as discomfort, and is associated with a 91% higher mortality rate compared to fistulas. In trying to increase the prevalence of fistulas in the U.S., a proportional rise in catheter use has been documented. What is needed is an improved vascular access device that addresses the foregoing problems.

BRIEF SUMMARY OF THE INVENTION

The present invention solves the foregoing problems by allowing a percutaneous connection to be created between an artery and vein in the arm of a kidney failure patient without the need for surgery; which allows immediate cannulation of the connection without reliance on catheter use; and which allows for the maturation of the outflow veins for subsequent conversion to a fistula.

In one aspect of the invention, an anastomotic connector is provided that comprises a generally tubular access port having a first end and a second end, a generally tubular main body portion having a first end and a second end, wherein the second end of the main body portion is positioned adjacent to the second end of the access port such that the main body portion and access port are in fluid communication, and an anchor member received within the access port and having a plurality of fingers that are extendable from the first end thereof. The fingers of the anchor member are movable between a loaded position wherein the fingers are substantially parallel to a center axis of the access port and an expanded position wherein the fingers are substantially perpendicular to the center axis of the access port.

In another aspect of the present invention, a method of positioning an anastomotic connector within a fluid passageway comprises the steps of: (i) providing an anastomotic connector including a generally tubular access port having a first end and a second end, a generally tubular main body portion having a first end and a second end, wherein the second end of the main body portion is positioned adjacent to the second end of the access port such that the main body portion and access port are in fluid communication, and an anchor member received within the access port and having a plurality of fingers that are extendable from the first end thereof; (ii) loading the anastomotic connector onto an introducer; (iii) introducing a distal end of the introducer through an access site in a fluid passageway; and (iv) deploying the access port and the anchor member into the fluid passageway, wherein upon deployment the fingers of the anchor member are expanded to engage an internal surface of the fluid passageway.

DETAILED DESCRIPTION OF THE INVENTION

Generally speaking, the invention is directed to an anastomotic connector structured to attach a dialysis graft between an artery and a vein. The anastomotic connectors in accordance with the invention may be placed percutaneously or subcutaneously in either an artery or a vein, and may be fabricated from any biocompatible material suitable for implantation into the human body. Further, the anastomotic connectors preferably have a low cost and are readily replaceable. As will be appreciated by those of ordinary skill in the art based upon the following disclosure, the anastomotic connectors of the invention may replace the use of catheters in those patients on hemodialysis who are permanently consigned to catheter use due to their inability (anatomically or otherwise) to sustain long-term fistula or graft options.

Numerous structural variations of an anastomotic connector device are contemplated and within the intended scope of the invention. For purposes of discussion and not limitation, one exemplary embodiment will be described in detail below. As those of ordinary skill in the art will appreciate, although the anastomotic connector will be described with reference to placement within a vessel, it should be understood that the anastomotic connectors may be placed within various other fluid passageways without departing from the intended scope of the invention.

Figure 1A:
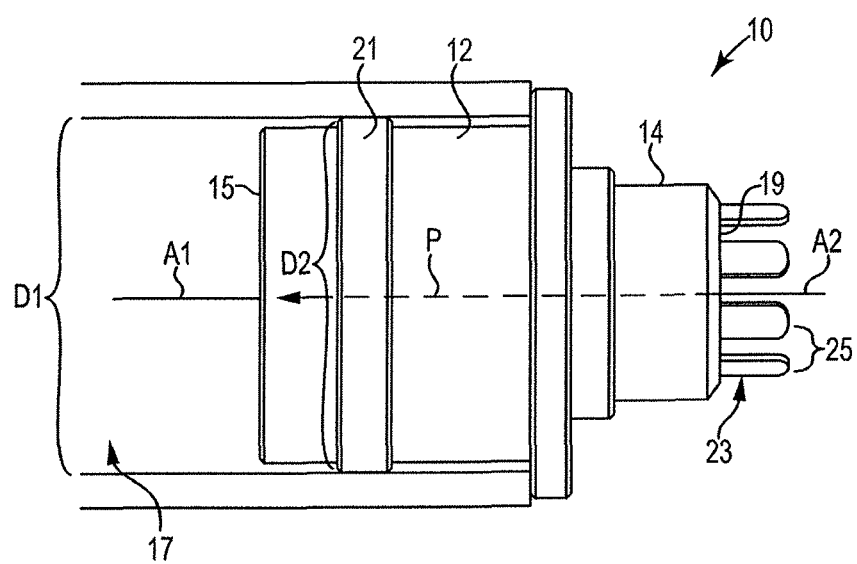
FIG. 1 is a side view of an exemplary embodiment of an anastomotic connector in accordance with the invention illustrating an anchor member in a non-deployed position.
Figure 1B:
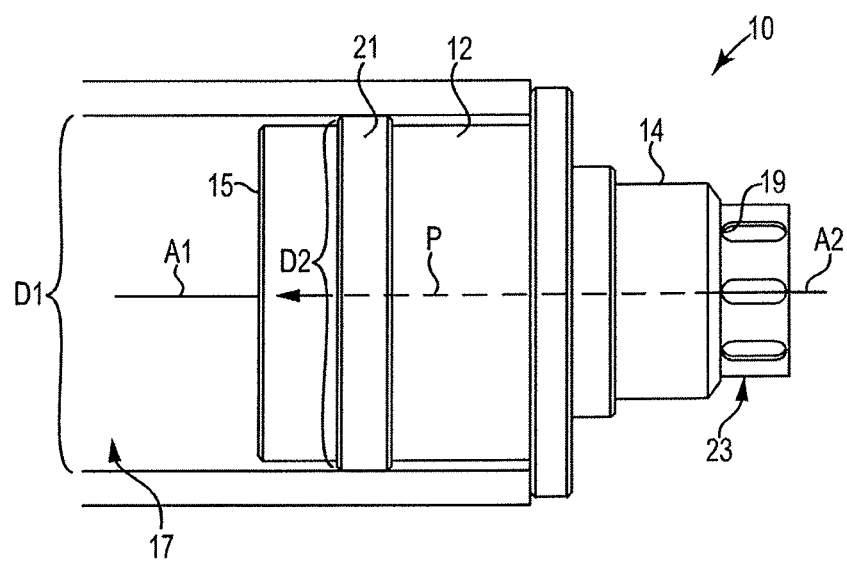
Figure 1C:
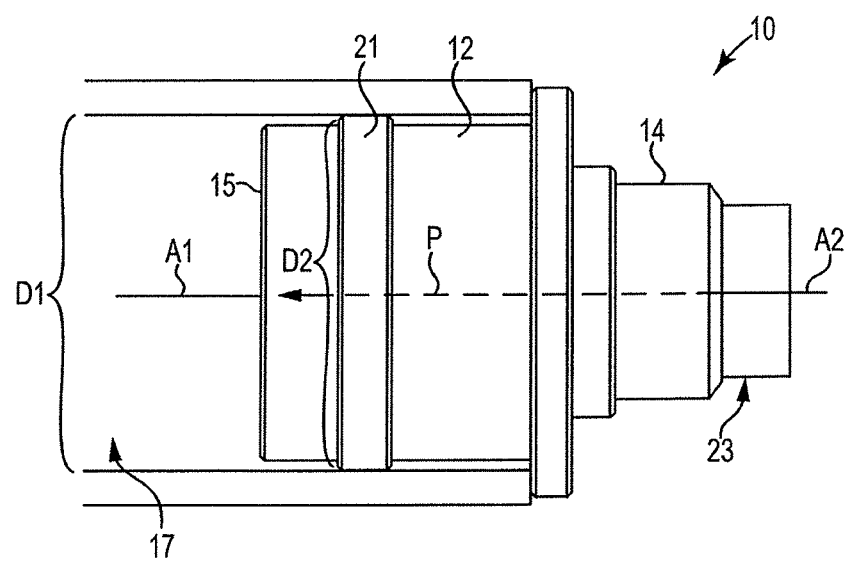

FIG. 1 is a side view of one exemplary embodiment of an anastomotic connector 10 in accordance with the invention. As illustrated in FIG. 1, anastomotic connector 10 generally includes a main body 12 and an access port 14 extending therefrom. A center axis A1 of main body 12 is substantially aligned with a center axis A2 of access port 14. Main body 12 includes an open first end 15 and access port 14 includes an open first end 19. An open second end of main body 12 is in fluid communication with an open second end of access port 14 thereby providing a fluid pathway P through anastomotic connector 10.

In one exemplary embodiment, an internal diameter of main body 12 may be greater than an internal diameter of access port 14. However, in other embodiments the internal diameter of main body 12 may be less than the internal diameter of access port 14, or the internal diameters may be substantially equivalent, without departing from the intended scope of the invention. The internal diameters of main body 12 and access port 14 may depend upon numerous factors such as, for example, the desired amount of flow through the connector 10. In exemplary embodiments the internal diameters of main body 12 and access port 14 may range between about 1 mm and about 10 mm, although larger or smaller internal diameters are also contemplated and within the intended scope of the invention.

As illustrated in FIG. 1, anastomotic connector 10 includes a tubular graft 17 operably coupled to and surrounding main body 12. Main body 12 includes a flange 21 extending around a circumference thereof. A first internal diameter D1 of graft 17 is sized substantially equivalent to or slightly smaller than a second external diameter D2 of flange 21 such that a fluid tight seal is formed between graft 17 and main housing 12.

Figure 2A:
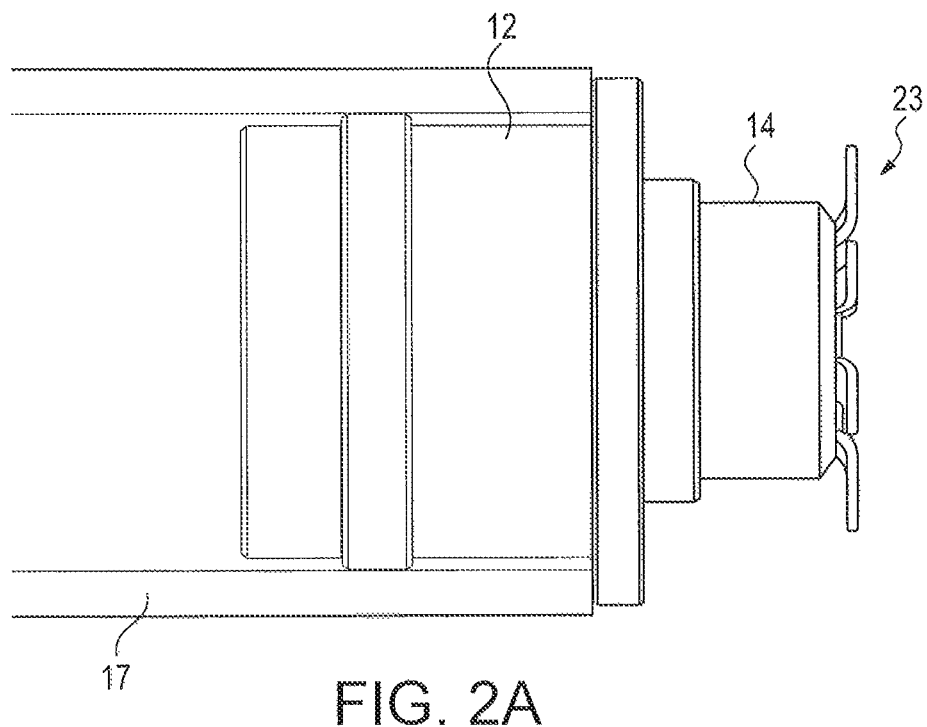
FIG. 2A is a side view of the anastomotic connector of FIG. 1 with an anchor member in an expanded or deployed position.
Figure 2B:
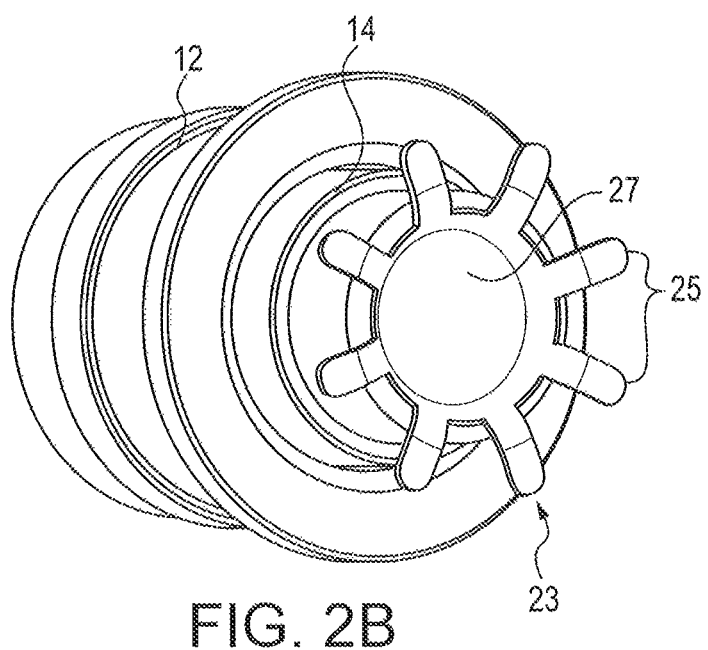
FIG. 2B is a perspective view of the anastomotic connector of FIG. 2A.

As further illustrated in the exemplary embodiment of FIG. 1, access port 14 includes anchor member 23 extending through open first end 19. Anchor member 23 includes a plurality of fingers 25 that are structured to move between a loaded position as illustrated in FIG. 1 and an expanded position as illustrated in FIGS. 2A and 2B (discussed in further detail below). As will be appreciated by those of ordinary skill in the art, anchor member 23 is structured to provide a secure, rigid connection to a vessel. Anchor member 23 may be either self-expanding or non self-expanding. One benefit of using a self-expanding material is that fingers 25 will expand when deployed within a vessel without the need for a separate expansion device, thus eliminating additional equipment and steps during the deployment process. On the other hand, one benefit of using a non self-expanding material is that a surgeon maintains control over the instant in time when fingers 25 are expanded and the precise degree to which the fingers 25 are expanded.

Exemplary "self-expanding" materials that may be used include, but are not limited to, shape memory alloys such as nitinol, stainless steel, or various polymers. Nitinol may be preferable due to its high yield strain. However, any suitable self-expanding material may be used as will be appreciated by those of ordinary skill in the art. Furthermore, although any suitable non self-expanding material may be used, exemplary materials may include stainless steel, titanium, or the like.

FIGS. 2A and 2B are side and perspective views, respectively, of anastomotic connector 10 with fingers 25 of anchor member 23 in an expanded position. As more clearly illustrated in FIG. 2B, anchor member 23 includes a tubular portion 27 that extends inwardly through open first end 19 of access port 14. Thus, in the illustrated embodiment, anchor member 23 is structured as a nitinol segment of tubing having fingers 25 formed at a distal end that protrude from access port 14.

Figure 3:
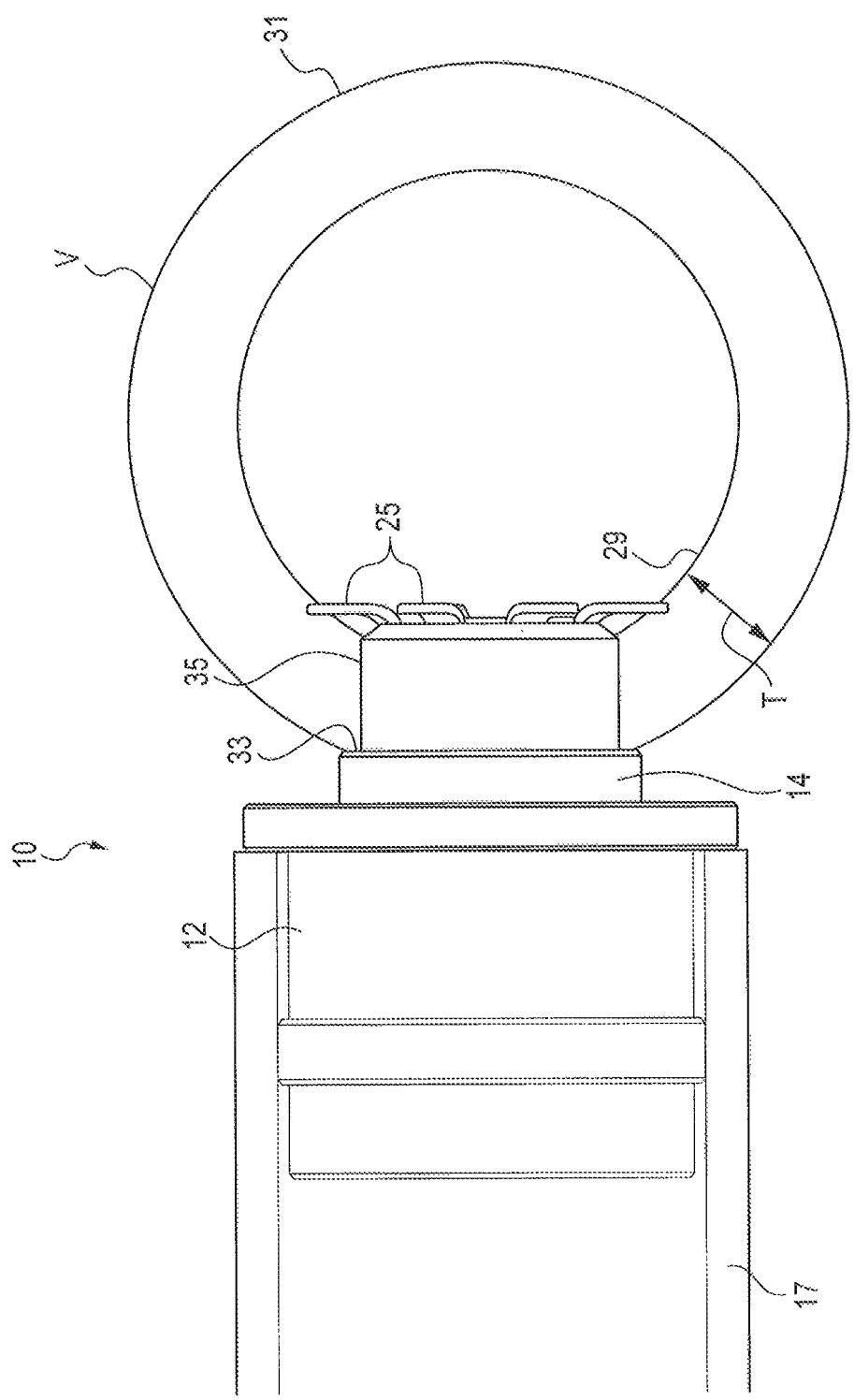
FIG. 3 is a diagram illustrating the expanded anchor member in engagement with an internal surface of a vessel.

FIG. 3 is a diagram illustrating anastomotic connector 10 deployed within a vessel V. Particularly, once anastomotic connector 10 is deployed within vessel V, fingers 25 of anchor member 23 are moved to the expanded position (either due to the shape memory properties or by mechanical actuation) to secure the connector 10 to vessel V. As shown in FIG. 3, in the expanded position fingers 25 engage an inner surface 29 of vessel V. In order to provide a fluid tight seal between anastomotic connector 10 and vessel V, access port 14 is provided with a first sealing surface 33 that is structured to engage with an outer surface 31 of vessel V and a second sealing surface 35 that is structured to engage with the vessel wall between inner surface 29 and outer surface 31. Preferably, second sealing surface 35 has a length that is substantially equivalent to or greater than a thickness T of vessel V. Furthermore, FIG. 3 illustrates first sealing surface 33 being substantially perpendicular to second sealing surface 35 merely for purposes of example and not limitation. Thus, other configurations are contemplated as will be appreciated by those of ordinary skill in the art.

Main body 12 and access port 14 of anastomotic connector 10 may be formed using any suitable biocompatible material as will be appreciated by those of ordinary skill in the art. Such biocompatible materials may include, but are not limited to, expanded Polytetrafluoroethylene ("ePTFE"), polyester, silicone composites, or various other plastics and elastomers or combinations thereof. Further, main body 12 and access port 14 may be formed using the same or different materials without departing from the intended scope of the invention.

Additionally, it may be preferable to provide the anastomotic connectors of the invention with an inner surface that is contoured to allow smooth arterial or venous blood flow into and out of the connector device. As those of ordinary skill in the art will appreciate, providing a non-thrombogenic surface minimizes the creation of recirculation or stagnation zones with high shear or dwell times that could otherwise lead to clotting.

It is also contemplated that the inner or outer surface of the connector be configured to deliver and release therapeutic substances such as anti-microbial agents, anti-inflammatory agents, anti-proliferative agents (e.g. taclipaxel), growth factors, stem cells, collagen and the like. Those of ordinary skill in the art will appreciate that these therapeutic agents may be coupled with the connector and/or the external or internal surface of the connector by means such as being encased or embedded in a polymeric or other biocompatible coating, applied to a textured external surface of the connector; contained within pockets of the connector on either an internal or external surface, and the like.

Although anchor member 23 is described as including "fingers" 25, other anchoring structures, such as hooks, barbs, tines and other types of curved or angled fasteners are contemplated as will be appreciated by those of ordinary skill in the art. For example, in the loaded position of FIG.

1 the expandable portion 23 may comprise a continuous expandable cylinder comprising a solid expandable material. The cylinder may optionally include hooks to secure it to the inner surface of a vessel wall. Alternatively, the expandable cylinder may include a plurality of slits around the circumference of the solid cylinder to facilitate expansion.

As will be discussed in further detail to follow, a first one of the anastomotic connectors 10 may be implanted through the sidewall of an artery in such a way that access port 14 protrudes through the sidewall at the site of implant. A second one of the anastomotic connectors 10 may be implanted through the sidewall of a vein in such a way that access port 14 protrudes through the sidewall at the site of implant. A dialysis or vascular access graft, such as graft 17, may be attached to the first and second anastomotic connectors to provide a fluid pathway between the vein and the artery. One exemplary but non-limiting type of graft that may be used is a Vectra® vascular access graft.

More particularly, in one exemplary method of positioning or deploying anastomotic connectors in accordance with the invention, the connectors may be deployed with a catheter type introducer mechanism. For example, a needle access aperture may first be made into the target artery through the intended implant site of the connector. A guidewire may then be guided through the inserted needle. Once the guidewire is fully inserted, the needle may be retracted while leaving the guidewire in position. Next, an introducer that is "pre-loaded" with an anastomotic connector may be slid over the guidewire. Once the anastomotic connector is positioned within the artery, the particular anchor member associated with the connector may be deployed. As will be appreciated by those of ordinary skill in the art, when non self-expanding anchor members are utilized, the introducer may include an expansion means.

Figure 4A:
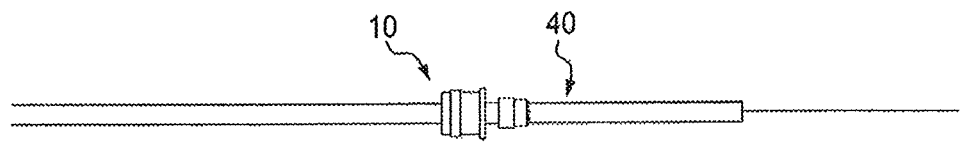
FIG. 4A is a perspective view of the anastomotic connector of FIG. 1 loaded on an introducer used in an exemplary method of deploying the anastomotic connector of FIG. 1.
Figure 4B:
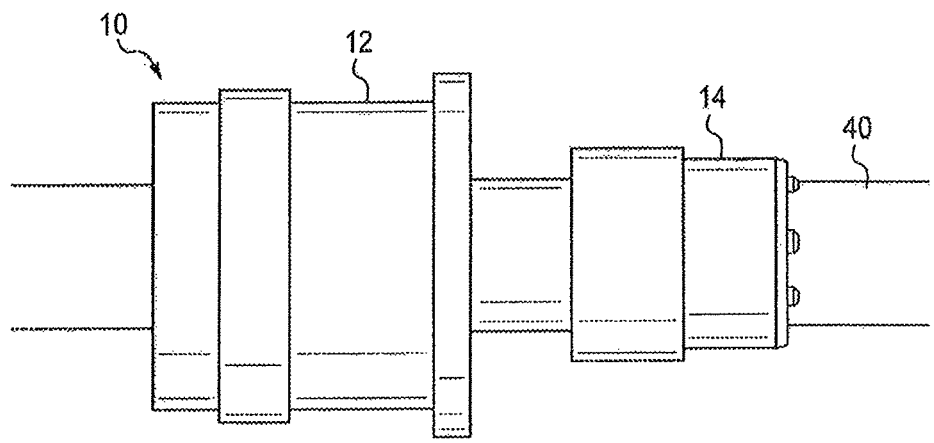
FIG. 4B is an enlarged view of FIG. 4A showing detail.
Figure 4C:
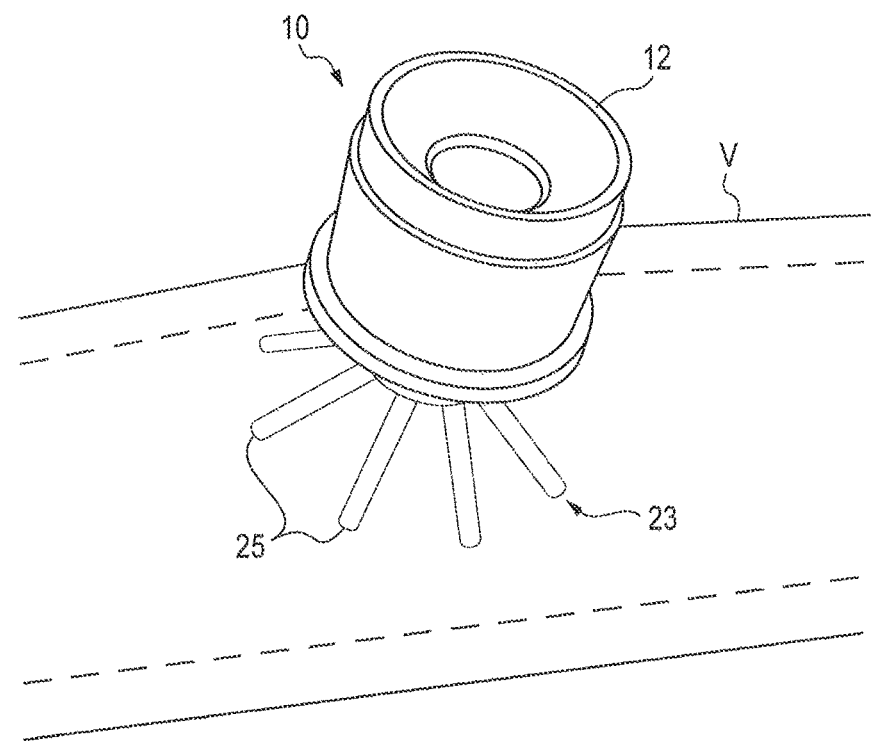
FIG. 4C is a perspective view of the anastomotic connector of FIG. 1 deployed in a vessel.
Figure 4D:
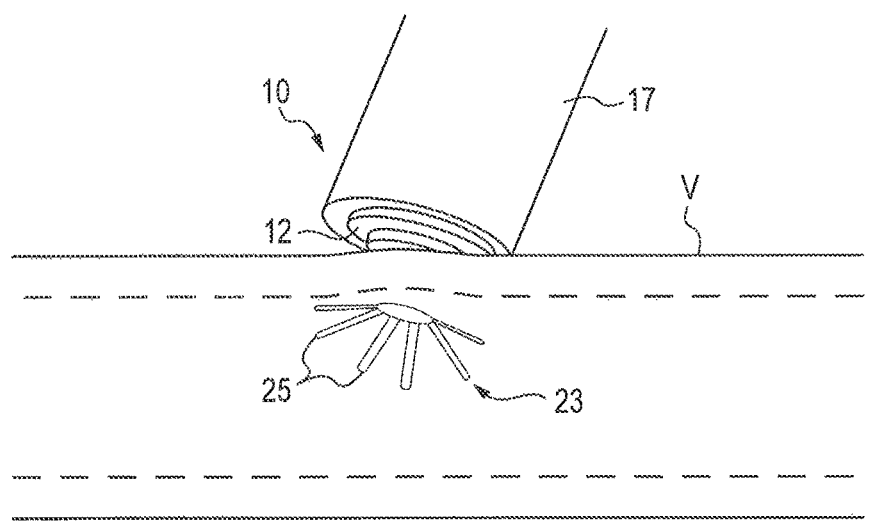
FIG. 4D is a perspective view of the anastomotic connector attached to a graft component in accordance with the invention.

Further details regarding an exemplary method of deploying an anastomotic connector in accordance with the invention are illustrated in FIGS. 4A-4D. Particularly, FIGS. 4A-4D illustrate the deployment of anastomotic connector 10 having a self-expanding anchor member 23. However, the exemplary deployment method is described with reference to anastomotic connector 10 merely for purposes of example and not limitation. Thus, workers of ordinary skill in the art will appreciate that various other embodiments of the invention may be deployed in a similar manner. As shown in FIGS. 4A and 4B, an introducer 40 is pre-loaded with anastomotic connector 10. The anastomotic connector 10 is then introduced into a target vessel V (post needle and guidewire insertion). As shown in FIGS. 4A and 4B, access port 14 is initially spaced apart from main body 12 when anastomotic connector 10 is pre-loaded onto introducer 40. During deployment into vessel V, access port 14 slides rearwardly until it is positioned adjacent to main body 12, thereby reducing or eliminating the gap between the components. FIG. 4C illustrates anastomotic connector 10 deployed within vessel V and introducer 40 withdrawn from the connector. Particularly, fingers 25 of anchor member 23 have "self-expanded" in FIG. 4C to anchor connector 10 to vessel V. While anastomotic connector 10 is being deployed, the physician may verify that the connector placement is accurate by feeling the resistance of the anchor member fingers 25 against the inner surface of the vessel wall. As will be appreciated by those of ordinary skill in the art, after deployment the engagement of the anchor member fingers 25 with the inner surface of the vessel V functions to securely maintain the anastomotic connector in fluid-tight engagement at the desired implantation site. Once anastomotic connector 10 has been properly secured to vessel V, the physician may attach graft 17 to main body 12 as illustrated in FIG. 4D.

As will be appreciated by those of ordinary skill in the art, the same general process illustrated in FIGS. 4A-4D may be followed in order to place a connector within other types of fluid passageways.

Although FIGS. 4A-4D generally illustrate a method of deploying an anastomotic connector having a self-expanding anchor member, the method may be adapted for deploying an anastomotic connector having a non self-expanding anchor member. For example, the fingers of the anchor member may be expanded against the inner surface of the vessel with an expansion means that is inserted through the access port. Once expanded, the fingers of the anchor member may be structured to engage and exert force on the vessel wall to provide a secure connection between the vessel and the anastomotic connector.

As will be appreciated by those of ordinary skill in the art, any suitable expansion means that is associated with or separate from the introducer may be used in accordance with the invention. In one exemplary embodiment, the expansion means may be a balloon expanding support structure. Furthermore, the balloon expanding support structure may be expanded by filling the interior portion of the support structure with, for example, air or a saline solution. Other suitable expansion means include, but are not limited to, dilators or stents.

Based upon the present disclosure and after viewing the exemplary embodiment of the anastomotic connector presented herein, the many advantages and benefits provided by the invention will be appreciated by those of ordinary skill in the art. One advantage is that the geometry of the anastomotic connector allows continuous and uninterrupted arterial or venous flow during use for dialysis or other applications, thereby eliminating or substantially reducing any loss of circulation to the downstream, distal extremities. Stated alternatively, the geometry of the anastomotic connectors allows "full" flow into the graft as well as "full" flow to the downstream anatomy. Thus, distal arterial flow is not "cut-off" due to the presence of the anastomotic connector. Another advantage is that the anastomotic connectors of the invention may be implanted percutaneously rather than with an "open surgery" approach. The implantation method is therefore less invasive for the patient and faster for the surgeon. Yet another advantage is that the present invention allows for maturation of the distal vein in preparation for secondary AVF while avoiding a central dialysis catheter.

Although the present invention has been described with reference to preferred embodiments, workers skilled in the art will recognize that changes may be made in form and detail without departing from the spirit and scope of the invention.

What is claimed is:

1. An anastomotic connector comprising:
a generally tubular main body portion having a proximal end and a distal end;
a generally tubular access port having a distal end and a proximal end, the tubular access port slidably coupled to said tubular main body and extending outwardly therefrom in a spaced-apart relationship, the proximal end of said access port being in fluid communication with the distal end of the tubular main body; and
an anchor member having first and second ends, said second end operably coupled to the distal end of said access port, said anchor member including an expandable portion that extends from the first end thereof, the expandable portion movable between a loaded position wherein the expandable portion is substantially parallel to a center axis of the access port and released position wherein the expandable portion is substantially perpendicular to the center axis of the access port, wherein upon placement in a vessel said tubular access port is configured to slide proximally to lie adjacent the tubular main body thereby eliminating the spaced-apart relationship.

2. The anastomotic connector of claim 1 wherein said tubular main body includes an internal diameter that is greater than an internal diameter of said access port.

3. The anastomotic connector of claim 1 wherein said tubular main body includes an internal diameter that is equal to an internal diameter of said access port.

4. The anastomotic connector of claim 1 wherein said access port includes an internal diameter that is greater than an internal diameter of said tubular main body.

5. The anastomotic connector of claim 1 wherein said anchor member comprises a segment of tubing formed from Nitinol.

6. The anastomotic connector of claim 1 wherein said expandable portion is formed at the first end of said anchor member and is configured to project outwardly from said access port in the loaded position.

7. The anastomotic connector of claim 6 wherein said first end of said anchor member is a distal end.

8. The anastomotic connector of claim 6 wherein the fingers are configured to engage an inner surface of a vessel wall in the expanded position.

9. The anastomotic connector of claim 1 wherein said access port includes a first sealing surface and a second sealing surface, said first sealing surface adapted to provide a fluid tight seal between the anastomotic connector and an outer surface of a vessel wall, and said second sealing surface is adapted to engage a vessel wall between an inner surface and said outer surface.

10. The anastomotic connector of claim 9 wherein the second sealing surface of the access port has a length that is greater than or equal to a thickness of the vessel wall.

11. The anastomotic connector of claim 9 wherein the first sealing surface is substantially perpendicular to the second sealing surface.

12. The anastomotic connector of claim 9 wherein the first sealing surface is co-axially disposed about the second sealing surface.

13. The anastomotic connector of claim 1 wherein a material that forms the anastomotic connector is selected from the group consisting of expanded Polytetrafluoroethylene, polyester, silicone, silicone composites, elastomers and combinations of the foregoing.

14. The anastomotic connector of claim 1 wherein a material that forms said access port is different that a material that forms the main body.

15. The anastomotic connector of claim 1 wherein an inner surface of said connector is contoured to allow smooth arterial or venous blood flow through said connector.

16. The anastomotic connector of claim 1 wherein an outer surface of said connector or an inner surface of said connector or both is configured to deliver and release therapeutic substances.

17. The anastomotic connector of claim 16 wherein said therapeutic substances are selected from the group consisting of anti-microbial agents, anti-inflammatory agents, anti-proliferative agents, taclipaxel, growth factors, stem cells, collagen and combinations of the foregoing.

18. The anastomotic connector of claim 16 wherein said therapeutic agents are coupled to an internal or external surface of said connector.

19. The anastomotic connector of claim 18 wherein said therapeutic agents are encased or embedded in a biocompatible coating applied to said internal or external surface.

20. The anastomotic connector of claim 1 wherein the expandable portion comprises a plurality of fingers positioned circumferentially about the first end of said access port in a spaced apart relationship one from the other.

21. The anastomotic connector of claim 1 wherein the expandable portion comprises a continuous cylinder.

22. The anastomotic connector of claim 21 wherein the continuous cylinder includes a plurality of slits around a circumference thereof.

23. The anastomotic connector of claim 1 wherein said expandable member comprises a material that is self-expandable.

24. A method of positioning the anastomotic connector of claim 1 within a fluid passageway comprising: providing the anastomotic connector of claim 1; loading the anastomotic connector onto an introducer; introducing a distal end of the introducer through an access site in a fluid passageway; deploying the access port and the anchor member into the fluid passageway; causing expansion of the anchor member against an inner surface of the fluid passageway.

25. The method of claim 24 further comprising causing the access port to slide proximally.

26. The method of claim 24 further comprising positioning said access port adjacent the tubular main body.

27. The method of claim 24 further comprising providing expansion means to cause the expansion of said expandable portion against said inner surface of the fluid passageway.

* * * * *

UNITED STATES PATENT AND TRADEMARK OFFICE
CERTIFICATE OF CORRECTION

PATENT NO. : 9,597,443 B2  
APPLICATION NO. : 14/119652  
DATED : March 21, 2017  
INVENTOR(S) : Yevzlin et al.

Page 1 of 1

It is certified that error appears in the above-identified patent and that said Letters Patent is hereby corrected as shown below:

On the Title Page

Item [56], insert:

--WO 2004-016201 A2   02-26-2004   COOK INCORPORATED

WO 2002-058594 A1   08-01-2002   SOLEM--

Signed and Sealed this  
Sixteenth Day of May, 2017

Michelle K. Lee  
*Director of the United States Patent and Trademark Office*